United States Patent
Gray et al.

(10) Patent No.: US 11,896,498 B2
(45) Date of Patent: Feb. 13, 2024

(54) INTERBODY FUSION DEVICES AND RELATED METHODS OF MANUFACTURE

(71) Applicant: MIRUS LLC, Atlanta, GA (US)

(72) Inventors: Wayne Gray, Atlanta, GA (US); Antonio Terrell, Atlanta, GA (US); Clint Walker, Atlanta, GA (US); Kevin R. Strauss, Atlanta, GA (US); Ryan O'Flaherty, Atlanta, GA (US); Noah Roth, Atlanta, GA (US)

(73) Assignee: MiRus LLC, Marietta, GA (US)

( * ) Notice: Subject to any disclaimer, the term of this patent is extended or adjusted under 35 U.S.C. 154(b) by 216 days.

(21) Appl. No.: 17/571,810

(22) Filed: Jan. 10, 2022

(65) Prior Publication Data
US 2022/0233330 A1      Jul. 28, 2022

Related U.S. Application Data

(63) Continuation of application No. 16/333,545, filed as application No. PCT/US2017/052019 on Sep. 18, 2017, now abandoned.
(Continued)

(51) Int. Cl.
*A61F 2/44*     (2006.01)
*A61F 2/30*     (2006.01)

(52) U.S. Cl.
CPC ............ *A61F 2/4465* (2013.01); *A61F 2/447* (2013.01); *A61F 2/4455* (2013.01); *A61F 2002/3006* (2013.01); *A61F 2002/3093* (2013.01); *A61F 2002/30154* (2013.01); *A61F 2002/30593* (2013.01); *A61F 2002/30677* (2013.01); *A61F 2002/30784* (2013.01);
(Continued)

(58) Field of Classification Search
CPC ...... A61F 2/4465; A61F 2/447; A61F 2/4455; A61F 2002/30838
USPC ............................................ 623/17.11–17.16
See application file for complete search history.

(56) References Cited

U.S. PATENT DOCUMENTS 7,488,444 B2    2/2009  Furst et al.
9,662,226 B2    5/2017  Wickham
(Continued)

OTHER PUBLICATIONS

International Search Report and Written Opinion, issued in the related international application No. PCT/US2017/052019 dated Nov. 17, 2017 (9 pages).
(Continued)

*Primary Examiner* — Eduardo C Robert
*Assistant Examiner* — Tara Rose E Carter
(74) *Attorney, Agent, or Firm* — Ulmer & Berne LLP; Brian E. Turung

(57) ABSTRACT

Interbody fusion devices and related methods of manufacture are described herein. An example interbody fusion device can include a plurality of vertebral endplates, and a body extending between the vertebral endplates. The body and the vertebral endplates can define an internal cavity. Additionally, each of the vertebral endplates can include a lattice structure and a frame surrounding the lattice structure, where the lattice structure being configured to distribute load. Each of the vertebral endplates can also include a plurality of micro-apertures having an average size between about 2 to about 10 micrometers (μm), and a plurality of macro-apertures having an average size between about 300 to about 800 micrometers (μm).

15 Claims, 5 Drawing Sheets

Related U.S. Application Data

(60) Provisional application No. 62/395,630, filed on Sep. 16, 2016.

(52) U.S. Cl.
CPC .............. *A61F 2002/30838* (2013.01); *A61F 2002/30904* (2013.01); *A61F 2310/00796* (2013.01)

(56) References Cited

U.S. PATENT DOCUMENTS

| | | |
|---|---|---|
| 9,687,358 B2 | 6/2017 | Bertele et al. |
| 9,848,995 B2 | 12/2017 | Ullrich, Jr. et al. |
| 2002/0153348 A1 | 10/2002 | Say et al. |
| 2003/0040798 A1 | 2/2003 | Michelson |
| 2006/0074490 A1 | 4/2006 | Sweeney |
| 2011/0035009 A1 | 2/2011 | Sweeney |
| 2011/0082551 A1 | 4/2011 | Kraus |
| 2011/0224796 A1 | 9/2011 | Weiland et al. |
| 2012/0172991 A1 | 7/2012 | Bertele et al. |
| 2012/0303127 A1* | 11/2012 | Ullrich, Jr. ............ A61F 2/3094 216/53 |
| 2012/0316653 A1 | 12/2012 | Ullrich, Jr. et al. |
| 2013/0116793 A1 | 5/2013 | Kloss |
| 2014/0100662 A1 | 4/2014 | Patterson et al. |
| 2014/0277491 A1 | 9/2014 | Fang et al. |
| 2015/0018958 A1 | 1/2015 | Ullrich, Jr. et al. |
| 2016/0270920 A1 | 9/2016 | Dawson et al. |
| 2016/0331543 A1 | 11/2016 | Butler et al. |
| 2017/0156880 A1 | 6/2017 | Halverson et al. |
| 2018/0071113 A1* | 3/2018 | Melkent ................ A61F 2/447 |

OTHER PUBLICATIONS

Pavon, J. et al., "Titanium scaffolds with multi-scale porosity obtained by controlled chemical and electrochemical treatments of porous solids from PM space holder technique," 10th World Biomaterials Congress Event Abstract, 2016 http://www.frontiersin.org/10.3389/conf.FBIOE.2016.01.02952/2893/10th_World_Biomaterials_Congress/all_events/event_abstract (accessed Sep. 7, 2017) (3 pages).

"FDA Clearance for Signus Mobisc (R) II ST interbody fusion device," SpinalSurgeryNews, 2015, http://www.spinalsurgerynews.com/2015/03/fda-clearance-for-signus_mobis-ii-st-interbody-fusion-device/9549 (accessed Sep. 7, 2017) (1 page).

* cited by examiner

INTERBODY FUSION DEVICES AND RELATED METHODS OF MANUFACTURE

CROSS-REFERENCE TO RELATED APPLICATIONS

This application is a continuation of U.S. application Ser. No. 16/333,545, filed Mar. 14, 2019, which is a national stage application filed under 35 U.S.C. § 371 of PCT/US2017/052019, filed Sep. 18, 2017, which claims the benefit of U.S. provisional patent application No. 62/395,630, filed on Sep. 16, 2016, and entitled "INTERBODY FUSION DEVICE," the disclosures of which are expressly incorporated herein by reference in their entireties.

FIELD

The interbody fusion devices disclosed herein pertain to the field of orthopedic surgery, and more specifically, spinal surgery.

BACKGROUND

Spinal abnormalities or disorders including, but not limited to lordosis (excessive inward curvature of the spine), kyphosis (excessive outward curvature of the spine), disk herniation, disk collapse, disk degeneration, or combinations thereof are caused by factors including trauma, disease, and/or degenerative conditions. These abnormalities or disorders can cause a patient to suffer discomfort, pain, deformity, and/or loss of mobility.

Surgical treatments are available to treat such spinal abnormalities or disorder. For example, spinal implants such as interbody fusion devices can be used to treat such abnormalities or disorders. As part of a surgical treatment, a spinal implant (e.g., interbody device) can be inserted into a patient's spine to provide stability. Interbody fusion devices can be introduced between vertebrae of the patient's spine (e.g., in the disk space between adjacent vertebrae) for fixation with bone to immobilize the joint as part of the surgical treatment.

SUMMARY

An example interbody fusion device is described herein. The interbody fusion device can include a plurality of vertebral endplates, and a body extending between the vertebral endplates. The body and the vertebral endplates can define an internal cavity. Additionally, each of the vertebral endplates can include a lattice structure and a frame surrounding the lattice structure, where the lattice structure is configured to distribute load. Each of the vertebral endplates can also include a plurality of micro-apertures having an average size between about 2 to about 10 micrometers (μm), and a plurality of macro-apertures having an average size between about 300 to about 800 micrometers (μm).

Additionally, the lattice structure can include a crisscrossed pattern of strips defining an array of openings. Each of the openings can extend between a contacting surface of one of the vertebral endplates and the internal cavity. Optionally, at least one of the openings can include an angled corner.

Alternatively or additionally, each of the vertebral endplates can include a plurality of teeth. For example, the teeth extend between respective lateral sides of the body. Optionally, the teeth can extend across the frame and the lattice structure.

Alternatively or additionally, the body can include an anterior end, a posterior end, and a pair of lateral sides extending between the anterior and posterior ends. In some implementations, the anterior end and the vertebral endplates define a tapered end. In some implementations, the posterior end can include an inserter attachment element. In some implementations, at least one of the lateral sides can include at least one support column extending between the vertebral endplates. In some implementations, at least one of the anterior end, the posterior end, or the lateral sides can include a window opening.

Alternatively or additionally, at least one of the micro-apertures or the macro-apertures can connect a contacting surface of one of the vertebral endplates to the internal cavity.

Alternatively or additionally, the body and the vertebral endplates are manufactured using a machining process.

Alternatively or additionally, the micro-apertures and the macro-apertures are manufactured using a chemical etching process.

Alternatively or additionally, the interior cavity can be configured to accept bone fusion material. Bone fusion material can include, but is not limited to, demineralized bone matrix (DBM), autograft bone, allograft bone, stem cells, or a synthetic material.

Alternatively or additionally, the vertebral endplates and the body can be formed of at least one of titanium or an alloy thereof, cobalt chrome alloy, stainless steel, molybdenum rhenium (MoRe), polyether ether ketone (PEEK), polyaryletherketone (PAEK), poly(methyl methacrylate) (PMMA), or carbon fiber.

Alternatively or additionally, the interbody fusion device can optionally include a fusion promoting or infection prevention coating layer provided on at least one of the vertebral endplates. Fusion promoting or infection prevention coating layer can include, but is not limited to, hydroxyapatite, a bone morphogenetic protein (BMP), an antibiotic, a porous coating, a hydrophilic coating, or silver zeolite.

An example method of manufacture is also described herein. The method can include forming from a material, using a machining process, an interbody fusion device including a plurality of vertebral endplates, and a body extending between the vertebral endplates, where the body and the vertebral endplates define an internal cavity. The method can also include forming from each of the vertebral endplates, using a machining process, a lattice structure and a frame surrounding the lattice structure, the lattice structure being configured to distribute load. The method can further include forming in each of the vertebral endplates, using a chemical etching process, a plurality of micro-apertures and a plurality of macro-apertures. The micro-apertures can have an average size between about 2 to about 10 micrometers (μm) and the macro-apertures can have an average size between about 300 to about 800 micrometers (μm).

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
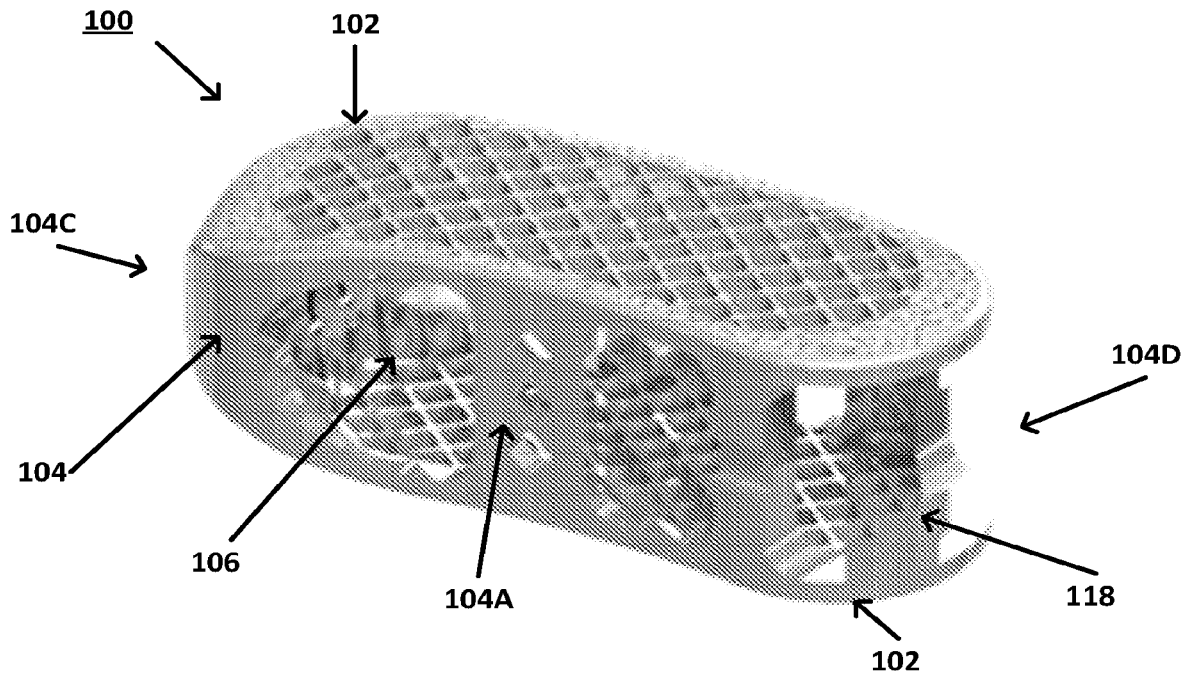
FIG. 1 is a perspective view of an interbody fusion device according to implementations described herein.
Figure 2:
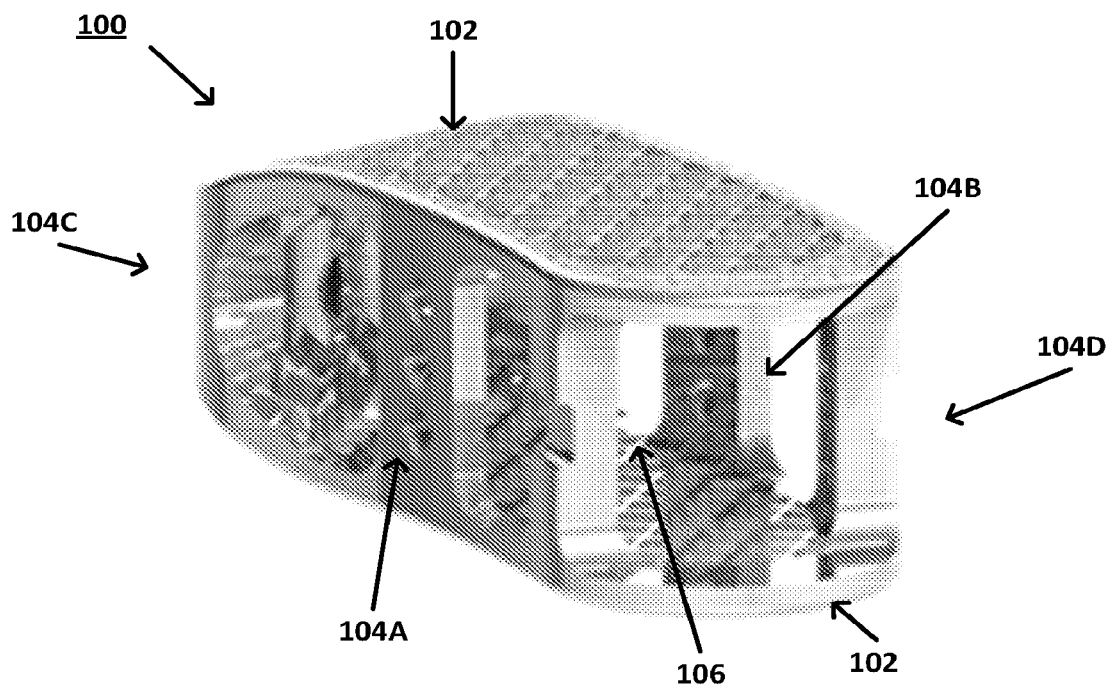
FIG. 2 is another perspective view of the interbody fusion device of FIG. 1.
Figure 3:
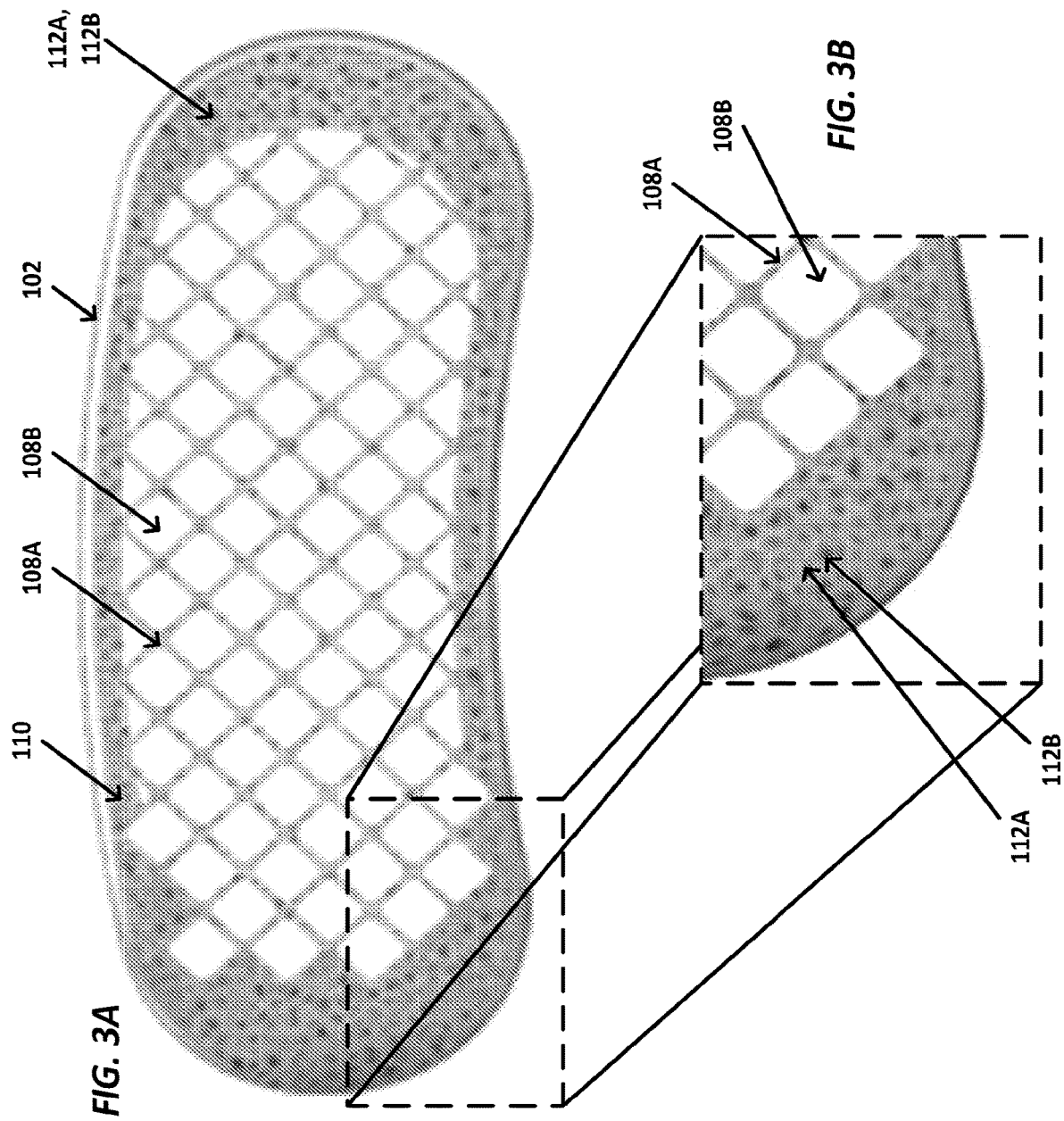
FIG. 3A is a top view of the interbody fusion device of FIG. 1.
FIG. 3B is an enlarged view of a portion of the interbody fusion device of FIG. 3A.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain, aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the ether particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Figure 6:
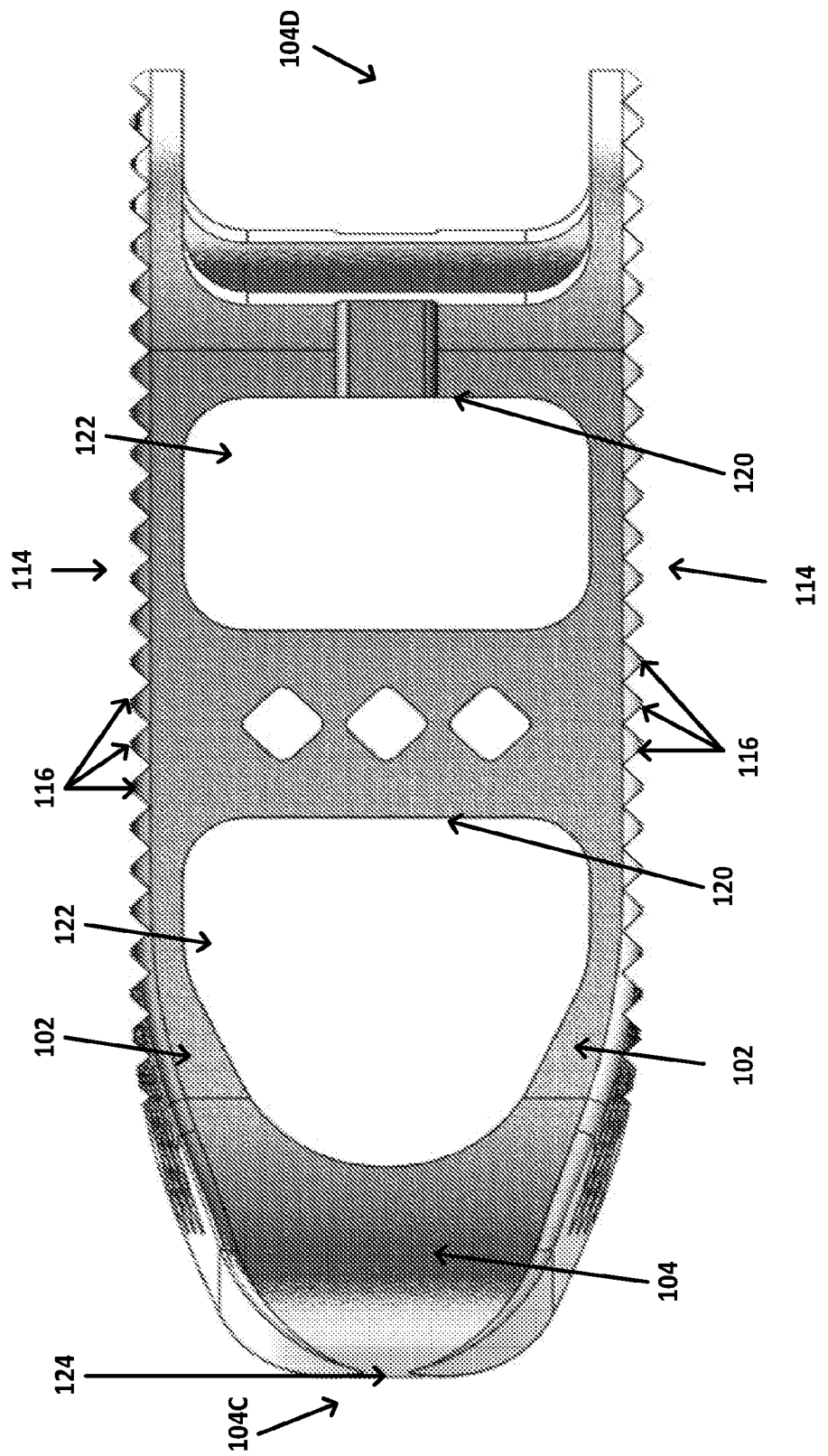
FIG. 6 is a side view of the interbody fusion device of FIG. 4.

Referring now to FIGS. 1-6, example interbody fusion devices (e.g., spinal implants) are shown. This disclosure contemplates that the example interbody fusion devices described herein can be used to treat various spinal disorders or abnormalities including, but not limited to, lordosis, kyphosis, disk herniation, disk collapse, disk degeneration, or combinations thereof. The interbody fusion devices described herein can be used for spinal joint fusion in the cervical, thoracic, lumbar, and/or sacral regions. The interbody fusion device 100 can include a plurality of vertebral endplates 102 and a body 104 extending between the vertebral endplates 102. Each of the vertebral endplates 102 is configured to interface or engage with bone (e.g., a vertebrae). As described below, a surface (e.g., contacting surface 114 as shown in FIG. 6) of the vertebral endplate 102 makes contact with a vertebrae when inserted in the patient's disk space, which is the space between adjacent vertebrae in the patient's spine. For example, one of the vertebral endplates 102 is configured to abut a lower surface of an upper vertebra and the other of the vertebral endplates 102 is configured to abut an upper surface of a lower vertebra that is adjacent the upper vertebra.

The body 104 can include a pair of lateral sides 104A and 104B, an anterior end 104C, and a posterior end 104D. As shown in the figures, the pair of lateral sides 104A and 104B extend between the anterior and posterior ends 104C and 104D, respectively. Additionally, the body 104 and the vertebral endplates 102 can define an internal cavity 106, e.g., an open space in a central region of the interbody fusion device 100. The interbody fusion device 100 is a semi-rectangular volumetric frame. It should be understood that the shape of the interbody fusion device 100 shown in the figures is provided only as an example and that interbody fusion devices can have shapes other than those described herein. The interior cavity 106 can be configured to accept bone fusion material. Bone fusion material can include, but is not limited to, demineralized bone matrix (DBM), autograft bone, allograft bone, stem cells, or a synthetic material. It should be understood that such materials can be used to promote fusion of the joint. Optionally, the interbody fusion device 100 can include a fusion promoting or infection prevention coating layer provided on at least one of the vertebral endplates 102. Fusion promoting or infection prevention coating layer can include, but is not limited to, hydroxyapatite, a bone morphogenetic protein (BMP), an antibiotic, a porous coating, a hydrophilic coating, or silver zeolite.

The interbody fusion device 100 can optionally formed from a metal alloy. For example, in some implementations, the interbody fusion device 100 is formed of molybdenum rhenium (MoRe). The use of MoRe in surgical instruments is described elsewhere, for example, in U.S. Pat. No. 7,488,444 to Furst et al., issued Feb. 10, 2009, and entitled "Metal alloys for medical devices"; U.S. Patent Application Publication No. 2016/0237541, published Aug. 18, 2016, and entitled "Improved Metal Alloy For Medical Devices"; and WO2017-003926 to Icon Medical Corporation, published Jan. 5, 2017, and entitled "Molybdenum alloys for medical devices", which are incorporated by reference in their entireties and for all purposes. The use of MoRe enables the design of smaller, less invasive components (e.g., equivalently-sized components with 2, 3, or 4 times the internal area for bone graft to be placed as compared to conventional components). MoRe as a material is highly resistant to fatigue, which enables the design of thinner walls. MoRe is not notch sensitive, which enables the design of sharp corners and angled surfaces. It should be understood that MoRe is only provided as one example metal alloy. This disclosure contemplates that the vertebral endplates 102 and the body 104 can be formed of other materials including, but not limited to, titanium or an alloy thereof, cobalt chrome alloy, stainless steel, polyether ether ketone (PEEK), polyaryletherketone (PAEK), poly(methyl methacrylate) (PMMA), or carbon fiber. This disclosure contemplates that the vertebral endplates 102 and/or the body 104 can be manufactured from the materials described above in solid form or powder/granular material as described below.

Each of the vertebral endplates 102 can include a lattice structure 108 and a frame 110 surrounding the lattice structure 108, where the lattice structure 108 is configured to distribute load. An example lattice structure 108 is shown in detail in FIGS. 3A and 3B. The lattice structure 108 can interface or engage with the patient's vertebrae when inserted in the patient's disk space. The lattice structure 108 can be configured to distribute load in similar manner to a "snowshoe" such that the vertebral endplates 102 resist subsidence. For example, the lattice structure 108 can include a crisscrossed pattern of strips 108A defining an array of openings 108B. As described herein, the lattice structure 108 can be formed using a machining process (e.g., a subtractive manufacturing process). Each of the openings 108B can have angled corners as shown in FIGS. 3A-3B. In other words, the openings 108B include substantially square corners. Using material such as MoRe, which is not notch sensitive, facilitates the ability to create angled surfaces in the lattice structure 108. This, disclosure contemplates that the openings 108B can be other shapes and/or sizes than those shown in the figures, which are provided only as examples. Each of the openings can extend between a contacting surface 114 of one of the vertebral endplates 102 and the internal cavity 106. It should be understood that material (e.g., bone fusion material), cells, tissue, and/or fluid can flow through the openings 108B. As described below, the body 104 and the vertebral endplates 102 can be manufactured using a machining process (or subtractive manufacturing process), e.g., the lattice structure 108 can be formed by machining.

Each of the vertebral endplates 102 can also include a plurality of micro-apertures 112A. Example micro-apertures 112A are shown in detail in FIGS. 3A and 3B. The micro-apertures 112A are configured to promote on-growth of bone. For example, micro-apertures 112A can have an average size between about 2 to about 10 micrometers (μm). One or more of the micro-apertures 112A can connect the contacting surface 114 of one of the vertebral endplates 102 to the internal cavity 106, i.e., the micro-apertures 112A can create channels through which bone can grow to facilitate spinal fusion. It should be understood that material (e.g., bone fusion material), cells, tissue, and/or fluid can flow through the micro-apertures 112A, which facilitates on-growth of bone. In some implementations, the micro-apertures 112A are homogeneous. In other implementations, the micro-apertures 112A have varying sizes and/or shapes (with the average size falling between about 2 μm to about 10 μm). The micro-apertures 112A can optionally be pattered and/or randomly located on the vertebral endplates 102.

Additionally, each of the vertebral endplates 102 can also include a plurality of macro-apertures 112B. Example macro-apertures 112B are shown in detail in FIGS. 3A and 3B. The macro-apertures 112B are configured to promote through-growth of bone. For example, macro-apertures 112B can have an average size between about 300 to about 800 micrometers (μm). One or more of the macro-apertures 112B can connect the contacting surface 114 of one of the vertebral endplates 102 to the internal cavity 106, the macro-apertures 112B can create channels through which bone can grow to facilitate spinal fusion. It should be understood that material (e.g., bone fusion material), cells, tissue, and/or fluid can flow through the macro-apertures 112B, which facilitates through-growth of bone. In some implementations, the macro-apertures 112B are homogeneous. In other implementations, the macro-apertures 112B have varying sizes and/or shapes (with the average size falling between about 300 μm to about 800 μm). The macro-apertures 112B can optionally be pattered and/or randomly located on the vertebral endplates 102.

In some implementations, the micro- and/or macro-apertures 112A, 112B can be provided such that the interbody fusion device 100 has a stiffness equal to or greater than cancellous bone. Alternatively or additionally, the interbody fusion device 100 can optionally have a composite porosity of 75-85% with 300-800 μm pores and 2-10% porosity with 10-50 μm pores. For comparison, cancellous bone has 75-85% porosity with 300-600 μm pores and cortical bone has 5-10% porosity with 10-50 μm pores.

By including micro- and macro-apertures 112A, 112B, highly porous vertebral endplate contacting surfaces (e.g., contacting surface 114 as shown in FIG. 6) are provided. Such porous vertebral endplates 102 facilitate spinal fusion. Porosity is achieved by providing a plurality of apertures (i.e., both micro- and macro-apertures 112A, 112B) that connect the contacting surface 114 to the internal cavity 106. As described below, the micro- and macro-apertures 112A, 112B can be manufactured using a chemical etching process.

Each of the vertebral endplates 102 can include a plurality of teeth 116. The teeth 116 can project from the vertebral endplate 102 toward the patient's vertebrae. In other words, the teeth 116 can be angular ridges with grooves there between. The teeth 116 can be configured to interface or engage with the vertebrae when inserted in the patient's disk space. The teeth 116 can provide resistance to movement when loaded and resist expulsion of the interbody fusion device 100 from the disk space before fusion is complete.

Figure 4:
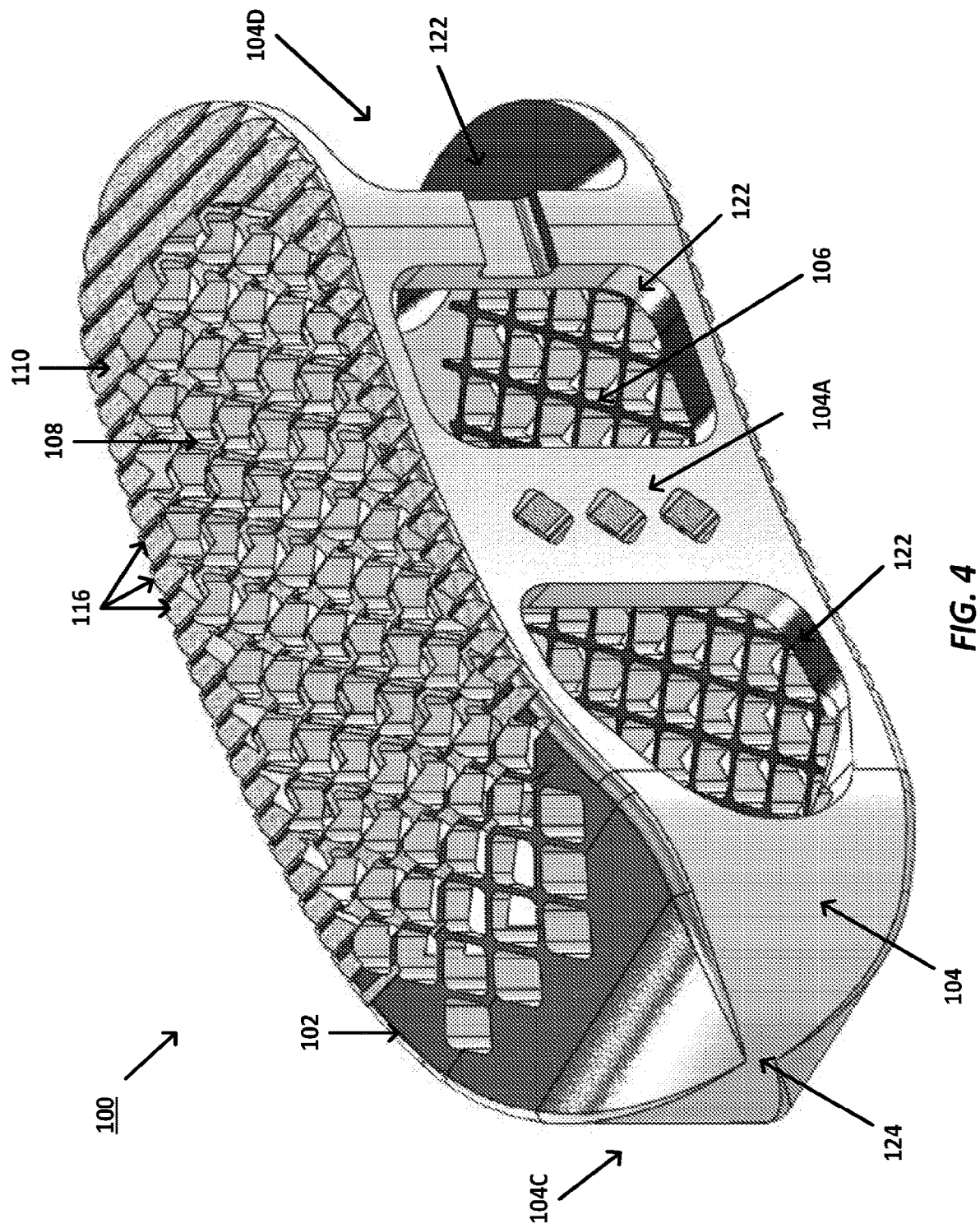
FIG. 4 is a perspective view of another interbody fusion device according to implementations described herein.
Figure 5:
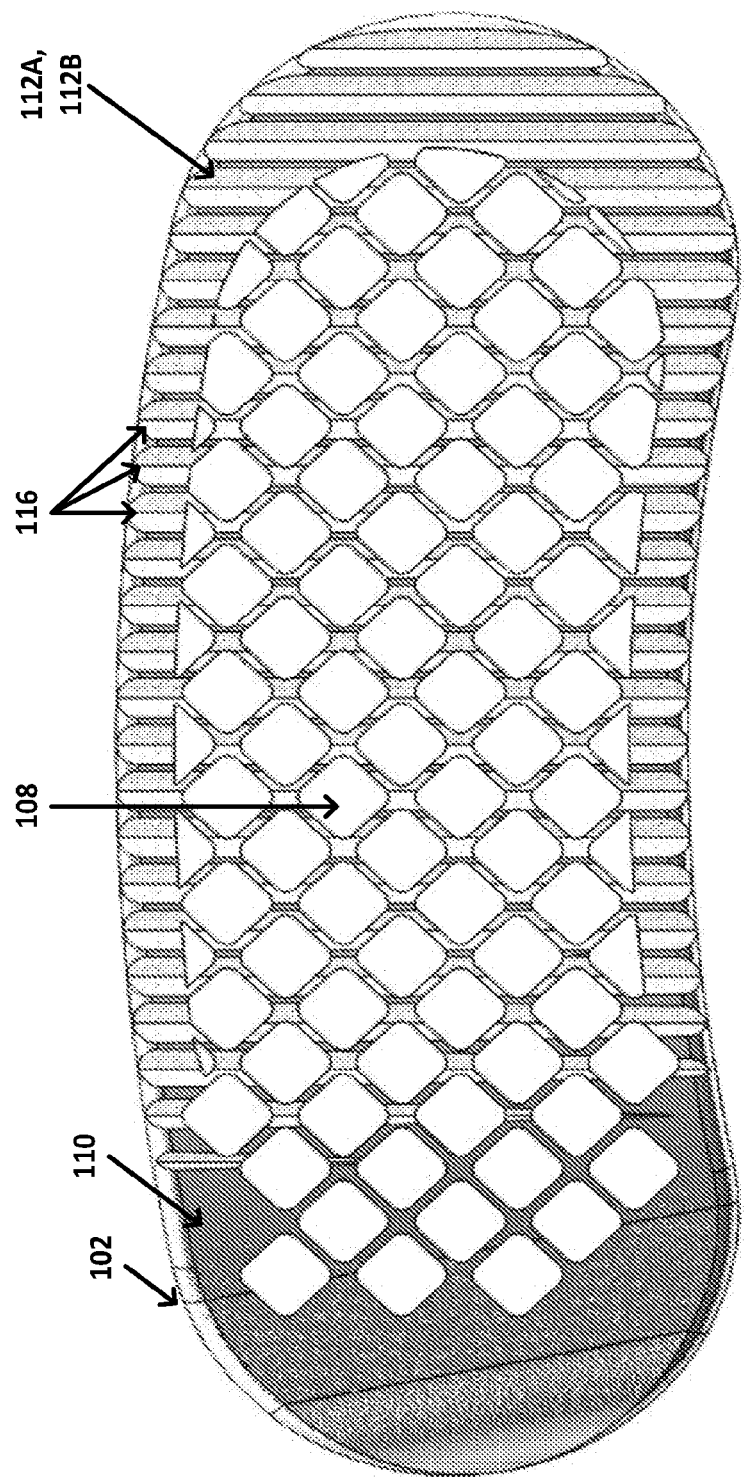
FIG. 5 is a top view of the interbody fusion device of FIG. 4.

The teeth 116 can extend between respective lateral sides 104A, 104B of the body 104. Optionally, the teeth 116 can extend across the frame 110 and the lattice structure 108 (e.g., as shown in FIG. 4). In other words, the ridges/grooves can extend across the frame 110 and through the lattice structure 108 from one side of the interbody fusion device 100 to the other side. As shown in the figures, the teeth 116 are arranged in parallel. It should be understood that the teeth 116 can have other configurations including, but not limited to, being arranged to converge/diverge, with regular or irregular spacing, with uniform or non-uniform patterns, etc.

In some implementations, the anterior end 104C and the vertebral endplates 102 define a tapered end 124. In other words, at least one portion of the interbody fusion device 100 can have a "bulleted" nose. The "bulleted" nose, with either open or closed end, facilitates insertion of the interbody fusion device 100 into the disk space (e.g., the collapsed space between two vertebrae). In some implementations, the vertebral endplates 102 can be angled with respect to one another (e.g., lordotic or kyphotic angle). For example, angled vertebral endplates can be used to facilitate surgical corrections of the patient's spine and/or restore natural anatomic positioning. In some implementations, the posterior end 104D can include an inserter attachment element 118. The inserter attachment element 118 can attach to a tool (e.g., surgical instrument) used for inserting the interbody fusion device 100 into the disk space. In some implementations, at least one of the lateral sides 104A, 104B can include at least one support column 120 extending between the vertebral endplates 102. The column 120 can provide rigidity. This disclosure contemplates that the number and/or arrangement of columns should not be limited by the examples shown in the figures. In some implementations, at least one of the anterior end 104C, the posterior end 104D, or the lateral sides 104A and 104B can include a window opening 122. The window openings 122 can be used for identification of bony growth inside the interbody fusion device 100 using medical imaging (e.g., x-ray, magnetic resonance imaging (MRI), computed tomography (CT), etc.). Optionally, the posterior end 104D can include a relative large window opening 122 (e.g., as shown in FIG. 4), which can be used for in-situ packing of bone fusion material (e.g., graft material). This disclosure contemplates that the number and/or arrangement of window openings should not be limited by the examples shown in the figures.

An example method of manufacture is also described herein. The method can include forming from a material, using a machining process, an interbody fusion device (e.g., interbody fusion device 100) including a plurality of vertebral endplates and a body extending between the vertebral endplates, where the body and the vertebral endplates define an internal cavity. The method can also include forming from each of the vertebral endplates, using a machining process, a lattice structure and a frame surrounding the lattice structure, the lattice structure being configured to distribute load. The method can further include forming in each of the vertebral endplates, using a chemical etching process, a plurality of micro-apertures and a plurality of macro-apertures. The micro-apertures can have an average size between about 2 to about 10 micrometers (μm) and the macro-apertures can have an average size between about 300 to about 800 micrometers (μm). The chemical etching process can include dipping each of the vertebral endplates in an acid such as nitric acid. This disclosure contemplates that the type of acid, acid concentration, and/or dipping parameters (e.g., temperature, time, etc.) can be selected to achieve the desired pore sizes.

Another example method of manufacture involves beginning with a non-spherical powder, which is poured into a mold. Using a press, the power can be formed into a solid using substantial pressure forming a green state part. The part can then sintered using extreme heat to bond the material together, then placed back in the mold. Using an even higher pressure, the almost finish product can be completed. The second use of pressure ensures densification of the material.

Although the subject matter has been, described in language, specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An interbody fusion device comprising top and bottom endplates, first and second lateral sides, anterior and posterior ends, and a body; said body positioned between said top and bottom endplates, said first and second lateral sides, and said anterior and posterior ends; each of said top and bottom endplates configured to interface or engage with bone when said interbody fusion device is positioned between adjacent vertebra of a spine; said body includes a body cavity; said first lateral side includes a plurality of first lateral openings that terminate in said body cavity; said second lateral side includes a plurality of second lateral openings that terminate in said body cavity; cavity; said posterior end includes a first posterior opening that terminates in said body cavity; said anterior end absent an opening that terminates in said body cavity; said top endplate is formed of a top lattice structure and a top frame surrounding said top lattice structure; said bottom endplate is formed of a bottom lattice structure and a bottom frame surrounding said bottom lattice structure; said top lattice structure on said top endplate forming a plurality of top openings that terminate in said body cavity; said bottom lattice structure on said bottom endplate forming a plurality of bottom openings that terminate in said body cavity; said top frame of said top endplate includes a top micro-aperture region that fully encircles said top lattice structure; said top micro-aperture region includes a plurality of top micro-apertures having an average size of 2-10 micrometers (μm) and a plurality of top macro-apertures having an average size of 300-800 micrometers (μm); one or more of said top micro-apertures terminating in said body cavity; one or more of said top macro-apertures terminating in said body cavity; each of said top openings has a size that is greater than each of said top micro-apertures and each of said top macro-apertures; said bottom frame of said bottom endplate includes a bottom micro-aperture region that fully encircles said bottom lattice structure; said bottom micro-aperture region includes a plurality of bottom micro-apertures having an average size of 2-10 micrometers (μm) and a plurality of bottom macro-apertures having an average size of 300-800 micrometers (μm); one or more of said bottom micro-apertures terminating in said body cavity; one or more of said bottom macro-apertures terminating in said body cavity; each of said bottom openings has a size that is greater than each of said bottom micro-apertures and each of said bottom macro-apertures.

2. The interbody fusion device as defined in claim 1, wherein a majority of said top openings has a same shape; and a majority of said bottom openings has a same shape.

3. The interbody fusion device as defined in claim 2, wherein a majority of said top openings has a square shape along a longitudinal length of said top opening; and a majority of said bottom openings has a square shape along a longitudinal length of said bottom opening.

4. The interbody fusion device as defined in claim 3, wherein a majority of said top openings include angled corners; and a majority of said bottom openings include angled corners.

5. The interbody fusion device as defined in claim 4, wherein each of said top and bottom endplates includes a plurality of teeth.

6. The interbody fusion device as defined in claim 5, wherein each of said first and second lateral sides has a curved profile along a complete longitudinal length of said first and second lateral sides; said anterior end has a curved profile along a complete width of said anterior end.

7. The interbody fusion device as defined in claim 6, wherein first posterior opening extends a full width of said posterior end.

8. The interbody fusion device as defined in claim 7, wherein said top and bottom endplates, said first and second lateral sides, and said anterior and posterior ends formed of one or more materials selected from the group consisting of a) demineralized bone matrix (DBM), b) autograft bone, c) allograft bone, d) stem cells, e) synthetic material; f) titanium; g) titanium alloy; g) cobalt chrome alloy; i) stainless steel; j) molybdenum rhenium (MoRe) alloy; k) polyether ether ketone (PEEK); l) polyaryletherketone (PAEK); m) poly(methyl methacrylate) (PMMA); and n) carbon fiber.

9. The interbody fusion device as defined in claim 8, wherein one or both of said top endplate and said bottom endplate includes a fusion promoting or infection prevention coating layer; said fusion promoting or infection prevention coating layer includes one or more materials selected form the group consisting of a) hydroxyapatite, b) bone morphogenetic protein (BMP), c) antibiotic, d) porous coating, e) hydrophilic coating, and f) silver zeolite.

10. The interbody fusion device as defined in claim 2, wherein a majority of said top openings include angled corners; and a majority of said bottom openings include angled corners.

11. The interbody fusion device as defined in claim 1, wherein each of said top and bottom endplates includes a plurality of teeth.

12. The interbody fusion device as defined in claim 1, wherein each of said first and second lateral sides has a curved profile along a complete longitudinal length of said first and second lateral sides; said anterior end has a curved profile along a complete width of said anterior end.

13. The interbody fusion device as defined in claim 1, wherein first posterior opening extends a full width of said posterior end.

14. The interbody fusion device as defined in claim 1, wherein said top and bottom endplates, said first and second lateral sides, and said anterior and posterior ends formed of one or more materials selected from the group consisting of a) demineralized bone matrix (DBM), b) autograft bone, c) allograft bone, d) stem cells, e) synthetic material; f) titanium; g) titanium alloy; g) cobalt chrome alloy; i) stainless steel; j) molybdenum rhenium (MoRe) alloy; k) polyether ether ketone (PEEK); l) polyaryletherketone (PAEK); m) poly(methyl methacrylate) (PMMA); and n) carbon fiber.

15. The interbody fusion device as defined in claim 1, wherein one or both of said top endplate and said bottom endplate includes a fusion promoting or infection prevention coating layer; said fusion promoting or infection prevention coating layer includes one or more materials selected form the group consisting of a) hydroxyapatite, b) bone morphogenetic protein (BMP), c) antibiotic, d) porous coating, e) hydrophilic coating, and f) silver zeolite.

* * * * *